United States Patent
Edwards et al.

(10) Patent No.: US 9,120,802 B2
(45) Date of Patent: *Sep. 1, 2015

(54) PYRIMIDINE DERIVATIVES AND THEIR USE IN THE TREATMENT OF RESPIRATORY DISEASES SUCH AS COPD

(75) Inventors: Christine Edwards, Harlow (GB); Janusz Kulagowski, Harlow (GB); Harry Finch, Slough (GB)

(73) Assignee: Chiesi Farmaceutici S.p.A., Parma (IT)

( * ) Notice: Subject to any disclaimer, the term of this patent is extended or adjusted under 35 U.S.C. 154(b) by 241 days.

This patent is subject to a terminal disclaimer.

(21) Appl. No.: 13/640,004

(22) PCT Filed: Mar. 10, 2011

(86) PCT No.: PCT/GB2011/050478
§ 371 (c)(1),
(2), (4) Date: Jan. 7, 2013

(87) PCT Pub. No.: WO2011/110859
PCT Pub. Date: Sep. 15, 2011

(65) Prior Publication Data
US 2013/0123278 A1    May 16, 2013

(30) Foreign Application Priority Data
Mar. 12, 2010 (GB) .................... 1004179.6

(51) Int. Cl.
C07D 487/04 (2006.01)
A61K 31/519 (2006.01)

(52) U.S. Cl.
CPC ..................... *C07D 487/04* (2013.01)

(58) Field of Classification Search
CPC .................................................... C07D 487/04
USPC ........................................ 544/262; 514/262.1
See application file for complete search history.

(56) References Cited

U.S. PATENT DOCUMENTS

2012/0004203 A1* 1/2012 Von Nussbaum et al. .... 514/171

FOREIGN PATENT DOCUMENTS

| DE | 10 2006 031 314 | 1/2008 |
| JP | 2012-514615 | 6/2012 |
| WO | 2008 135537 | 11/2008 |

OTHER PUBLICATIONS

U.S. Appl. No. 13/640,001, filed Oct. 8, 2012, Edwards, et al.
U.S. Appl. No. 13/613,952, filed Sep. 13, 2012, Blench, et al.
International Search Report issued Jul. 27, 2011 in PCT/GB11/580478, filed Mar. 10, 2011.
Office Action dated Feb. 20, 2015 issued in Japanese patent application No. 2012-556588 (with English translation).
U.S. Appl. No. 14/571,755, filed Dec. 16, 2014, Alcaraz, et al.

* cited by examiner

*Primary Examiner* — Susanna Moore
(74) *Attorney, Agent, or Firm* — Oblon, McClelland, Maier & Neustadt, L.L.P.

(57) ABSTRACT

Compounds of formula (I) are inhibitors of neutrophil elastase, wherein A is C—$R^1$ or N; —$X^1$—$X^2$— is $CR^{15}$=N— or —$NR^{19}$—CO—; and $R^1$-$R^6$, $R^{15}$ and $R^{16}$ are as defined in the claims.

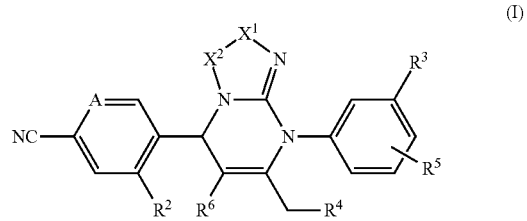

(I)

9 Claims, No Drawings

PYRIMIDINE DERIVATIVES AND THEIR USE IN THE TREATMENT OF RESPIRATORY DISEASES SUCH AS COPD

FIELD OF THE INVENTION

This invention relates to heterocyclic compounds, which are pyrimidine derivatives having human neutrophil elastase inhibitory properties, and their use in therapy.

BACKGROUND TO THE INVENTION

Human neutrophil elastase (HNE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (Bieth, G. In *Regulation of Matrix accumulation*, Mecham, R. P. (Eds), Academic Press, NY, USA 1986, 217-306). HNE has long been considered to play an important role in homeostasis through repair and disposal of damaged tissues via degradation of the tissue structural proteins. It is also relevant in the defense against bacterial invasion by means of degradation of the bacterial body. In addition to its effects on matrix tissues, HNE has been implicated in the upregulation of IL-8 gene expression and also induces IL-8 release from the epithelial cells of the lung. In animal models of Chronic Obstructive Pulmonary Disease induced by tobacco smoke exposure both small molecule inhibitors and protein inhibitors of HNE inhibit the inflammatory response and the development of emphysema (Wright, J. L. et al. *Am. J. Respir. Crit. Care Med.* 2002, 166, 954-960; Churg, A. et al. *Am. J. Respir. Crit. Care Med.* 2003, 168, 199-207). Thus, HNE may play a role both in matrix destruction and in amplifying inflammatory responses in chronic respiratory diseases where neutrophil influx is a characteristic feature. Indeed, HNE is believed to play a role in several pulmonary diseases, including chronic obstructive pulmonary disease (COPD), cystic fibrosis (CF), acute respiratory distress syndrome (ARDS), pulmonary emphysema, pneumonia and lung fibrosis. It is also implicated in several cardiovascular diseases in which tissue remodelling is involved, for example, in heart failure and the generation of ischaemic tissue injury following acute myocardial infarction.

COPD is an umbrella term encompassing three different pathological conditions, all of which contribute to limitation of airflow: chronic bronchitis, emphysema and small-airway disease. Generally all three will exist to varying extents in patients presenting with COPD, and all three may be due to neutrophil-mediated inflammation, as supported by the increased number of neutrophils observed in bronchoalveolar leakage (BAL) fluids of COPD patients (Thompson, A. B.; Daughton, D.; et al. *Am. Rev. Respir. Dis.* 1989, 140, 1527-1537). The major pathogenic determinant in COPD has long been considered to be the protease-anti-protease balance (also known as the 'elastase:anti-elastase hypothesis'), in which an imbalance of HNE and endogenous antiproteases such as α1-antitrypsin (α₁-AT), secretory leukocyte protease inhibitor (SLPI) and pre-elafin leads to the various inflammatory disorders of COPD. Individuals that have a genetic deficiency of the protease inhibitor α1-antitrypsin develop emphysema that increases in severity over time (Laurrell, C. B.; Erikkson, S Scand. *J. Clin. Invest.* 1963 15, 132-140). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

BRIEF DESCRIPTION OF THE INVENTION

This invention provides novel compounds which are inhibitors of HNE, and are useful in the treatment of diseases or conditions in which HNE activity plays a part.

DETAILED DESCRIPTION OF THE INVENTION

In one embodiment, the invention provides a compound of formula (I):

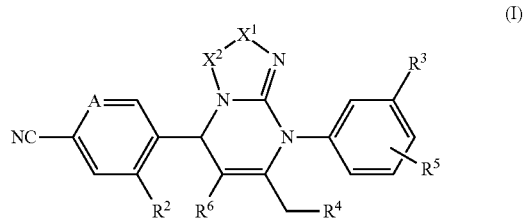

wherein

A is C—$R^1$ or N;

$R^1$ and $R^2$ are selected from hydrogen, halogen, nitro, cyano, —S(O)$_n R^7$, amino, mono- or di-$C_1$-$C_6$-alkylamino, —NHCOR$^8$, —NH(C=O)NHR$^9$, —NHSO$_2R^{10}$, $C_1$-$C_6$-alkyl, $C_2$-$C_6$-alkenyl, $C_2$-$C_6$-alkynyl, hydroxyl, $C_1$-$C_6$-alkoxy or $C_2$-$C_6$-alkenyloxy wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy;

n is 0, 1 or 2;

$R^4$ is hydrogen;

$R^3$ and $R^5$ are independently selected from hydrogen, halogen and $C_1$-$C_6$-alkyl which can be further substituted with halogen;

$R^6$ is selected from hydrogen, nitrile (—CN), —COOH, —COOR$^A$, —COR$^A$, —SO$_2R^A$, CONH$_2$, —SO$_2$NH$_2$, —CONHR$^A$, —SO$_2$NHR$^A$, —CONR$^A R^B$, —SO$_2$NR$^A R^B$, and heteroaryl, wherein R$^A$ and R$^B$ are independently an optionally substituted ($C_1$-$C_6$)alkyl, phenyl or monocyclic heteroaryl having 5 or 6 ring atoms, or R$^A$ and R$^B$ when attached to the same nitrogen atom form a cyclic amino ring;

$R^7$ is selected from $C_1$-$C_6$-alkyl, hydroxy-$C_1$-$C_6$-alkyl, $C_1$-$C_4$-alkoxy, amino, mono- or di-$C_1$-$C_4$-alkylamino, hydroxycarbonyl, aminocarbonyl, $C_3$-$C_6$-cycloalkyl, phenyl or $C_2$-$C_6$-alkenyl; wherein $C_3$-$C_6$-cycloalkyl can be substituted with one or more of $C_1$-$C_4$-alkyl, hydroxyl and $C_1$-$C_4$-alkoxy and phenyl can be substituted with one or more of halogen, cyano, $C_1$-$C_4$-alkyl, difluoromethyl, trifluoromethyl, difluoromethoxy, trifluoromethoxy and $C_1$-$C_4$-alkoxy;

$R^8$ and $R^9$ are independently selected from hydrogen and $C_1$-$C_6$-alkyl, and $R^{10}$ is $C_1$-$C_6$-alkyl;

—$X^1$—$X^2$— is —CR$^{15}$=N—, or —NR$^{19}$—CO—;

$R^{15}$ and $R^{19}$ each independently represent a radical of formula —[Y]$_m$-[Alk$^1$]$_p$-[Q]$_r$-[Alk$^2$]$_q$-Z, wherein Y is —O—, —S—, —NR$^E$—, —(C=O)—, —S(O)$_2$—, —C(=O)O—, —(C=O)NR$^E$—, —NR$^E$ (C=O)—, —NR$^E$—$C_1$-$C_4$-alkyl-, or —$C_1$-$C_4$-alkyl-NR$^E$—, —S(O)$_2$NR$^E$—, —NR$^E$S(O)$_2$— wherein R$^E$ is hydrogen, C$_1$-C$_6$ alkyl;

m, p, q and t are independently 0 or 1;

Alk$^1$ and Alk$^2$ each independently represent a C$_1$-C$_6$ alkylene radical;

Q represents a divalent mono- or bicyclic carbocyclic or heterocyclic radical having 3-9 ring members;

Z is (i) a monocyclic heterocyclic ring of 5 or 6 ring members or a bridged heterocyclic ring system of 7 or 8 ring members, wherein the ring heteroatoms are nitrogen, said monocyclic ring or bridged ring system being linked to the rest of the molecule via a ring carbon, and wherein a ring nitrogen may be quaternised by substitution by C$_1$-C$_3$ alkyl or benzyl the latter being optionally substituted in the phenyl ring thereof; or (ii) —N(R$^A$)(R$^B$) wherein R$^A$ and R$^B$ are independently hydrogen, or a C$_1$-C$_6$-alkyl, C$_3$-C$_6$-cycloalkyl group, or a phenyl(C$_1$-C$_6$)alkyl- group optionally substituted in the phenyl ring thereof; or, taken together with the nitrogen to which they are attached form a monocyclic heterocyclic ring of 5 to 7 ring atoms which may contain a further heteroatom selected from N, O and S; or (iii) —N$^+$(R$^A$)(R$^B$)(R$^C$) wherein R$^A$, R$^B$ and R$^C$ are independently a C$_1$-C$_6$-alkyl, C$_3$-C$_6$-cycloalkyl group, or a phenyl(C$_1$-C$_6$)alkyl- group optionally substituted in the phenyl ring thereof; or R$^A$ is a C$_1$-C$_6$-alkyl, C$_3$-C$_6$-cycloalkyl group, or a phenyl (C$_1$-C$_6$)alkyl- group optionally substituted in the phenyl ring thereof and R$^B$ and R$^C$ taken together with the nitrogen to which they are attached form a monocyclic heterocyclic ring of 5 to 7 ring atoms which may contain a further heteroatom selected from N, O and S; or R$^A$, R$^B$ and R$^C$ taken together with the nitrogen to which they are attached form a bridged heterocyclic ring system of 7 or 8 ring members;

(iv) —NR$^A$C(=NR$^B$)NR$^C$R$^D$ wherein

R$^A$, R$^B$, R$^C$ and R$^D$ are independently hydrogen or C$_1$-C$_6$-alkyl; or any two of R$^A$, R$^B$, R$^C$ and R$^D$ are independently hydrogen or C$_1$-C$_6$-alkyl, while the other two taken together represent a C$_1$-C$_6$ alkylene radical; or (v) —C(=NR$^A$)NR$^B$R$^C$, wherein R$^A$, R$^B$ and R$^C$ are independently hydrogen or C$_1$-C$_6$- alkyl; or any one of R$^A$, R$^B$ and R$^C$ is hydrogen or C$_1$-C$_6$-alkyl, while the other two taken together represent a C$_1$-C$_6$ alkylene radical;

(vi) —NR$^A$C(=NR$^C$)R$^B$, wherein

R$^A$, R$^B$ and R$^C$ are independently hydrogen or C$_1$-C$_6$- alkyl; or any one of R$^A$, R$^B$ and R$^C$ is hydrogen or C$_1$-C$_6$-alkyl, while the other two taken together represent a C$_1$-C$_6$ alkylene radical;

provided that R$^{15}$ is not (i) hydrogen or (ii) C$_1$-C$_6$ alkyl optionally substituted by hydroxy, C$_1$-C$_6$ alkoxy, C$_3$-C$_6$ cycloalkyl or fluoro or (iii) C$_1$-C$_6$ alkoxy or C$_1$-C$_6$ alkoxycarbonyl, (iv) C$_3$-C$_6$ cycloalkyl optionally substituted by C$_1$-C$_4$ alkyl or fluoro or (v) phenyl or 5- or 6-membered heteroaryl optionally substituted by fluoro, chloro, cyano, C$_1$-C$_4$ alkyl, difluoromethyl, trifluoromethyl, C$_1$-C$_4$ alkoxy, difluoromethoxy or trifluoromethoxy or (vi) —SO$_2$—NR$^x$R$^y$ or —NR$^a$R$^b$ where R$^x$ and R$^y$ are independently hydrogen, C$_1$-C$_6$ alkyl, C$_3$-C$_6$ cycloalkyl, phenyl or 5- or 6-membered heteroaryl and R$^a$ and R$^b$ are independently hydrogen, C$_1$-C$_6$ alkyl, C$_3$-C$_6$ cycloalkyl, C$_1$-C$_6$ alkyl, wherein in R$^x$, R$^y$, R$^a$ and R$^b$C$_1$-C$_6$ alkyl may be optionally substituted by cyano, hydroxy, C$_1$-C$_4$ alkoxy, hydroxycarbonyl, C$_1$-C$_4$ alkoxycarbonyl, aminocarbonyl, mono- or di-C$_1$-C$_4$ alkaminocarbonyl, C$_3$-C$_6$ cycloalkyl, phenyl or fluoro and wherein in R$^x$, R$^y$, R$^a$ and R$^b$ cycloalkyl may be optionally substituted by C$_1$-C$_4$ alkyl or fluoro and phenyl may be optionally substituted by fluoro, chloro, cyano, C$_1$-C$_4$ alkyl, difluoromethyl, trifluoromethyl, C$_1$-C$_4$ alkoxy, difluoromethoxy or trifluoromethoxy.

Compounds of formula (I) above thereof may be prepared in the form of salts, particularly pharmaceutically acceptable salts, N-oxides, hydrates and solvates thereof. Any claim to a compound herein, or reference to "compounds of the invention", "compounds with which the invention is concerned", "compounds of formula (I)", and the like includes such compounds whether or not in salt, N-oxide, hydrate or solvate form.

Compounds of the invention may be used in the treatment or prevention of diseases in which HNE is implicated, for example chronic obstructive pulmonary disease (COPD), chronic bronchitis, lung fibrosis, pneumonia, acute respiratory distress syndrome (ARDS), pulmonary emphysema, smoking-induced emphysema and cystic fibrosis.

Hence other aspects of the invention are (i) a pharmaceutical composition comprising a compound of the invention and a pharmaceutically acceptable carrier or excipient; and (ii) the use of a compound of the invention for the manufacture of a medicament for the treatment or prevention of a disease or condition in which HNE is implicated.

TERMINOLOGY

As used herein, the term "C$_a$-C$_b$-alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "C$_a$-C$_b$-alkenyl" wherein a and b are integers refers to a straight or branched chain alkenyl moiety having from a to b carbon atoms having at least one double bond of either E or Z stereochemistry where applicable. Thus when a is 2 and b is 6, for example, the term includes, for example, vinyl, allyl, 1- and 2-butenyl and 2-methyl-2-propenyl.

As used herein the term "C$_a$-C$_b$-alkynyl" wherein a and b are integers refers to straight chain or branched chain hydrocarbon groups having from a to b carbon atoms and having in addition one triple bond. Thus when a is 1 and b is 6, for example, the term includes for example, ethynyl (—C≡CH), 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent C$_a$-C$_b$-alkylene radical" wherein a and b are integers refers to a saturated hydrocarbon chain having from a to b carbon atoms and two unsatisfied valences.

As used herein the term "divalent C$_a$-C$_b$-alkenylene radical" wherein a and b are integers refers to a divalent hydrocarbon chain having from a to b carbon atoms, and at least one double bond.

As used herein the unqualified term "carbocyclic" refers to a mono-, bi- or tricyclic radical or bridged monocyclic or bicyclic radical having up to 16 ring atoms, all of which are carbon, and includes aryl and cycloalkyl. A bridged carbocyclic radical has a monocyclic or bicyclic ring with two ring atoms joined by an alkylene bridge, such as radicals of bicyclo[2.2.2]octane, bicyclo[3.1.1]heptane and adamantane.

As used herein the unqualified term "cycloalkyl" refers to a monocyclic saturated carbocyclic radical having from 3-8 carbon atoms and includes, for example, cyclopropyl, cyclobutyl, cyclopentyl, cyclohexyl, cycloheptyl, cyclooctyl, bicyclo[2.2.2]octanyl and adamantanyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl. Where a heteroaryl ring contains an sp2 nitrogen such as in the case of pyridine or imidazole, that nitrogen may be a quaternary nitrogen as in pyridinium or imidazolium.

As used herein the unqualified term "heterocyclyl" or "heterocyclic" or "heterocycloalkyl" includes "heteroaryl" as defined above, and in its non-aromatic meaning relates to a mono-, bi- or tri-cyclic or bridged monocyclic or bicyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. A bridged heterocyclic radical has a monocyclic or bicyclic ring containing at least one S, N or O ring atom with two ring atoms, such as two ring carbons, or a ring nitrogen and a ring carbon, joined by an alkylene bridge, such as radicals of 1-aza-bicyclo[2.2.2]octane. Where a ring nitrogen is bridged in this way, it may be further substituted as a quaternary nitrogen centre. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido, succinimido and 1-aza-bicyclo[2.2.2]octanyl or 1 methyl-1-aza-bicyclo[2.2.2]octanyl groups.

Unless otherwise specified in the context in which it occurs, the term "substituted" as applied to any moiety herein means substituted with up to four compatible substituents, each of which independently may be, for example, $C_1$-$C_6$-alkyl, cycloalkyl, $C_1$-$C_6$-alkoxy, hydroxy, hydroxyl-$C_1$-$C_6$-alkyl, mercapto, mercapto-$C_1$-$C_6$-alkyl, $C_1$-$C_6$-alkylthio, phenyl, monocyclic heteroaryl having 5 or 6 ring atoms, halo (including fluoro, bromo and chloro), trifluoromethyl, trifluoromethoxy, nitro, nitrile (—CN), oxo, —COOH, —COOR$^G$, —COR$^G$, —SO$_2$R$^G$, —CONH$_2$, —SO$_2$NH$_2$, —CONHR$^G$, —SO$_2$NHR$^G$, —CONR$^G$R$^H$, —SO$_2$NR$^G$R$^H$, —NH$_2$, —NHR$^G$, —NR$^G$R$^H$, —OCONH$_2$, —OCONHR$^G$, —OCONR$^G$R$^H$, —NHCOR$^G$, —NHCOOR$^G$, —NR$^H$COOR$^G$, —NHSO$_2$OR$^G$, —NR$^H$SO$_2$OH, —NR$^H$SO$_2$OR$^G$, —NHCONH$_2$, —NR$^G$CONH$_2$, —NHCONHR$^H$, —NR$^G$CONHR$^H$, —NHCONR$^G$R$^H$, or —NR$^G$CONR$^G$R$^H$ wherein R$^G$ and R$^H$ are independently a $C_1$-$C_6$-alkyl, $C_3$-$C_6$-cycloalkyl, phenyl or monocyclic heteroaryl having 5 or 6 ring atoms, or R$^G$ and R$^H$ when attached to the same nitrogen atom form a cyclic amino ring, such as piperidinyl, morpholinyl or piperazinyl. An "optional substituent" may be one of the foregoing substituent groups.

As used herein the term "salt" includes base addition and acid addition salts Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like. Those compounds (I) which have a quaternary nitrogen can also form quaternary salts with a pharmaceutically acceptable counter-ion such as chloride, bromide, acetate, formate, p-toluenesulfonate, succinate, hemi-succinate, naphthalene-bis sulfonate, methanesulfonate, xinafoate, and the like.

Compounds of the invention which contain one or more actual or potential chiral centres, because of the presence of asymmetric carbon atoms, can exist as a number of diastereoisomers with R or S stereochemistry at each chiral centre. The invention includes all such diastereoisomers and mixtures thereof.

In the compounds of the invention of formula (I), in any compatible combination:

The ring containing A is a phenyl or 3-pyridyl ring.

$R^1$ and $R^2$ are selected from any of the substituent types for which they are defined in relation to formula (I), including hydrogen, halogen such as fluoro and chloro, nitro, cyano, —S(O)$_2$(C$_1$-C$_3$alkyl) such as methanesulfonyl, amino, mono- or di-$C_1$-$C_6$-alkylamino such as methylamino and dimethylamino, —NHCOCH$_3$, —NH(C=O)NHCH$_3$, —NHSO$_2$CH$_3$, $C_1$-$C_6$-alkyl such as methyl, ethyl or n- or iso-propyl, $C_2$-$C_6$-alkenyl such as vinyl or allyl, $C_2$-$C_6$-alkynyl such as CH≡C—, hydroxyl, $C_1$-$C_6$-alkoxy such as methoxy or ethoxy or $C_2$-$C_6$-alkenyloxy such as allyloxy, wherein $C_1$-$C_6$-alkyl and $C_1$-$C_6$-alkoxy can be further substituted with one to three identical or different radicals selected from the group consisting of halogen such as fluoro, hydroxy and $C_1$-$C_4$-alkoxy.

In one type of compound of the invention, the ring containing A is phenyl, $R^1$ is hydrogen, and $R^2$ is hydrogen or 2-methanesulphonyl. In another type, the ring containing A is 3-pyridyl and $R^2$ is hydrogen or 2-methanesulphonyl.

$R^3$ and $R^5$ too may be selected from any of the substituent types for which they are defined in relation to formula (I), such as hydrogen, fluoro, chloro or bromo, and $C_1$-$C_6$-alkyl such as methyl which can be further substituted with halogen as in the case of trifluoromethyl. In one currently preferred type of compound of the invention $R^5$ is hydrogen and $R^3$ is 3-trifluoromethyl, 3-chloro or 3-bromo.

$R^6$ is selected from hydrogen, nitrile (—CN), —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, and heteroaryl, wherein R$^A$ and R$^B$ are independently an optionally substituted (C$_1$-C$_6$)alkyl, phenyl or monocyclic heteroaryl having 5 or 6 ring atoms, or R$^A$ and R$^B$ when attached to the same nitrogen atom form a cyclic amino ring.

In one type of compound of the invention, $R^6$ is —COOR$^A$, wherein R$^A$ is $C_1$-$C_4$ alkyl such as methyl, ethyl or isopropyl. —X$^1$—X$^2$— is —CR$^{15}$=N—, or —NR$^{19}$—CO— wherein R$^{15}$ and R$^{19}$ each independently represent a radical of formula —[Y]$_m$-[Alk$^1$]$_p$-[Q]$_t$-[Alk$^2$]$_q$-Z. In the radical —[Y]$_m$-[Alk$^1$]$_p$-[Q]$_t$-[Alk$^2$]$_q$-Z:

Y is —O—, —S—, —NR$^E$—, —(C=O)—, —S(O)$_2$—, —C(=O)O—, —(C=O)NR$^E$—, —NR$^E$(C=O)—, —NR$^E$—C$_1$-C$_4$-alkyl-, or —C$_1$-C$_4$-alkyl-NR$^E$—, —S(O)$_2$NR$^E$—, —NR$^E$S(O)$_2$— wherein R$^E$ is hydrogen or $C_1$-$C_6$ alkyl such as methyl;

m, p, q and t are independently 0 or 1;

Alk$^1$ and Alk$^2$ each independently represent a $C_1$-$C_6$ alkylene radical such as —CH$_2$—, —CH$_2$CH$_2$— or —CH$_2$CH$_2$CH$_2$—;

Q represents a divalent mono- or bicyclic carbocyclic or heterocyclic radical having 3-9 ring members, such as a 1,3-cyclopentylene, 1,4-cyclohexylene, 1-4-phenylene, 2,5-pyridinylene, 1,4-piperidinylene, or 1,4-piperazinylene radical;

Z is (i) a monocyclic nitrogen heterocycle of 5 or 6 ring members such as a pyridyl or imidazolyl ring or a bridged nitrogen heterocyclic system of 7 or 8 ring members such as a 1-aza-bicyclo[2.2.2]octane ring, said monocyclic ring or bridged ring system being linked to the rest of the molecule via a ring carbon, and wherein a ring nitrogen may be quaternised by substitution by $C_1$-$C_3$ alkyl such as methyl, by phenyl or by benzyl the latter being optionally substituted in the phenyl ring thereof; or (ii) —N(R$^A$)(R$^B$) wherein R$^A$ and R$^B$ are independently hydrogen, or a $C_1$-$C_6$-alkyl group such as methyl, ethyl or n- or isopropyl, a $C_3$-$C_6$-cycloalkyl group such as cyclopropyl, cyclopentyl or cyclohexyl, or a phenyl($C_1$-$C_6$)alkyl- group such as benzyl, optionally substituted in the phenyl ring thereof; or, taken together with the nitrogen to which they are attached form a monocyclic heterocyclic ring of 5 to 7 ring atoms which may contain a further heteroatom selected from N, O and S, such as a piperidine, piperazine or morpholine ring; or (iii) —N$^+$(R$^A$)(R$^B$)(R$^C$) wherein R$^A$, R$^B$ and R$^C$ are independently a $C_1$-$C_6$-alkyl group such as methyl, ethyl or n- or isopropyl, a $C_3$-$C_6$-cycloalkyl group such as cyclopropyl, cyclopentyl or cyclohexyl, or a phenyl($C_1$-$C_6$)alkyl- group such as benzyl, optionally substituted in the phenyl ring thereof; or R$^A$ is a $C_1$-$C_6$-alkyl group such as methyl, ethyl or n- or isopropyl, a $C_3$-$C_6$-cycloalkyl group such as cyclopropyl, cyclopentyl or cyclohexyl, or a phenyl($C_1$-$C_6$) alkyl- group such as benzyl, optionally substituted in the phenyl ring thereof and R$^B$ and R$^C$ taken together with the nitrogen to which they are attached form a monocyclic heterocyclic ring of 5 to 7 ring atoms which may contain a further heteroatom selected from N, O and S, such as a piperidine, piperazine or morpholine ring; or R$^A$, R$^B$ and R$^C$ taken together with the nitrogen to which they are attached form a bridged heterocyclic ring system of 7 or 8 ring members;

(iv) —NR$^A$C(=NR$^B$)NR$^C$R$^D$ wherein

R$^A$, R$^B$, R$^C$ and R$^D$ are independently hydrogen or $C_1$-$C_6$-alkyl such as methyl; or any two of R$^A$, R$^B$, R$^C$ and R$^D$ are independently hydrogen or $C_1$-$C_6$-alkyl, while the other two taken together represent a $C_1$-$C_6$ alkylene radical such as —CH$_2$—, —CH$_2$CH$_2$— or —CH$_2$CH$_2$CH$_2$—; or (v) —C(=NR$^A$)NR$^B$R$^C$, wherein R$^A$, R$^B$ and R$^C$ are independently hydrogen or $C_1$-$C_6$-alkyl such as methyl; or any one of R$^A$, R$^B$ and R$^C$ is hydrogen or $C_1$-$C_6$-alkyl such as methyl, while the other two taken together represent a $C_1$-$C_6$ alkylene radical such as —CH$_2$—, —CH$_2$CH$_2$— or —CH$_2$CH$_2$CH$_2$—; or (vi) —NR$^A$C(=NR$^C$)R$^B$, wherein R$^A$, R$^B$ and R$^C$ are independently hydrogen or $C_1$-$C_6$-alkyl such as methyl; or any one of R$^A$, R$^B$ and R$^C$ is hydrogen or $C_1$-$C_6$-alkyl such as methyl, while the other two taken together represent a $C_1$-$C_6$ alkylene radical such as —CH$_2$—, —CH$_2$CH$_2$— or —CH$_2$CH$_2$CH$_2$—.

In the radical —[Y]$_m$-[Alk$^1$]$_p$-[Q]$_t$-[Alk$^2$]$_q$-Z, the -[Alk$^1$]$_p$-[Q]$_t$-[Alk$^2$]$_q$- part may be selected from structures (IV) and (V) wherein V$^1$ and V$^2$ are each independently 0, 1, 2, 3 or 4 and X is a divalent mono- or bicyclic carbocyclic or heterocyclic radical having 3-9 ring members such as 1,4-cyclohexylene, 1,3 cyclopentylene, 1,4 phenylene, or 2,4 pyridinylene, and the Z part may be selected from structures (VI)-(XVI) wherein R$^A$, R$^B$, R$^C$, and R$^D$ are as defined in relation to formula (I), and V$^1$, V$^2$, and V$^3$ are each independently 0, 1, 2, 3 or 4.

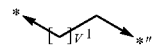

(IV)

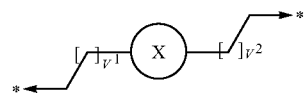

(V)

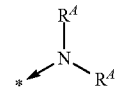

(VI)

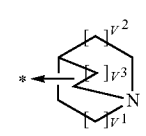

(VII)

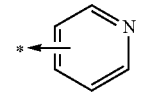

(VIII)

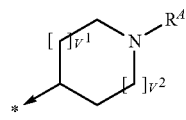

(IX)

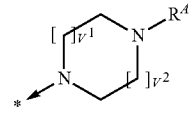

(X)

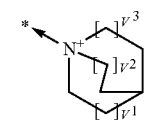

(XI)

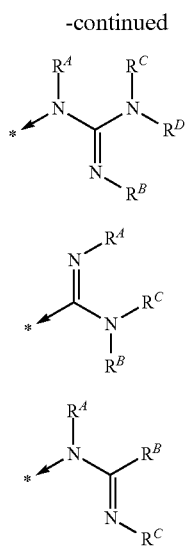

(XII)

(XIII)

(XIV)

Amine and pyridine nitrogen atoms, where present in groups (VI)-(XIV), may be quaternised with an optionally substituted $C_1$-$C_6$-alkyl or benzyl group.

In one type of compound of the invention, $R^{15}$ and $R^{19}$ each independently represent a radical of formula $-[Y]_m$-$Alk^2$-$Z$, wherein Y is $-(C=O)-$; m is 0 or 1; $Alk^2$ is a $C_1$-$C_6$ alkylene radical such as $-CH_2-$, $-CH_2CH_2-$ or $-CH_2CH_2CH_2-$; and Z is $-N(R^A)(R^B)$ wherein $R^A$ and $R^B$ are independently $C_1$-$C_4$-alkyl, such as methyl or ethyl, or $R^A$ is hydrogen and $R^B$ is $C_1$-$C_4$-alkyl, such as methyl, ethyl or isopropyl.

Examples of specific groups $R^1$-$R^6$ include those present in the compounds of the Examples herein.

The therapeutic utility of the present compounds is pertinent to any disease that is known to be at least partially mediated by the action of human neutrophil elastase. For example, the present compounds may be beneficial in the treatment of chronic obstructive pulmonary disease (COPD), cystic fibrosis (CF), acute respiratory distress syndrome (ARDS), pulmonary emphysema, pneumonia and lung fibrosis.

The present invention is also concerned with pharmaceutical formulations comprising, as an active ingredient, a compound of the invention. Other compounds may be combined with compounds of this invention for the prevention and treatment of inflammatory diseases of the lung. Thus the present invention is also concerned with pharmaceutical compositions for preventing and treating inflammatory diseases of the lung comprising a therapeutically effective amount of a compound of the invention and one or more other therapeutic agents.

Suitable therapeutic agents for a combination therapy with compounds of the invention include: (1) a corticosteroid, for example fluticasone or budesonide; (2) a β2-adrenoreceptor agonist, for example salmeterol or formeterol; (3) a leukotriene modulator, for example montelukast or pranlukast; (4) anticholinergic agents, for example selective muscarinic-3 (M3) receptor antagonists such as tiotropium bromide; (5) phosphodiesterase-IV (PDE-IV) inhibitors, for example roflumilast or cilomilast; (6) an antitussive agent, such as codeine or dextramorphan; and (7) a non-steroidal anti-inflammatory agent (NSAID), for example ibuprofen or ketoprofen.

The weight ratio of the first and second active ingredients may be varied and will depend upon the effective dose of each ingredient. Generally, an effective dose of each will be used.

The magnitude of prophylactic or therapeutic dose of a compound of the invention will, of course, vary with the nature of the severity of the condition to be treated and with the particular compound and its route of administration, and will generally be determined by clinical trial as required in the pharmaceutical art. It will also vary according to the age, weight and response of the individual patient. In general, the daily dose range will lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

Another aspect of the present invention provides pharmaceutical compositions which comprise a compound of the invention and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the invention, additional active ingredient(s), and pharmaceutically acceptable excipients.

The pharmaceutical compositions of the present invention comprise a compound of the invention as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Any suitable route of administration may be employed for providing a mammal, especially a human, with an effective dosage of a compound of the present invention. In therapeutic use, the active compound may be administered by any convenient, suitable or effective route. Suitable routes of administration are known to those skilled in the art, and include oral, intravenous, rectal, parenteral, topical, ocular, nasal, buccal and pulmonary (by inhalation).

Compositions suitable for administration by inhalation are known, and may include carriers and/or diluents that are known for use in such compositions. The composition may contain 0.01-99% by weight of active compound. Preferably, a unit dose comprises the active compound in an amount of 1 μg to 10 mg.

The most suitable dosage level may be determined by any suitable method known to one skilled in the art. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease undergoing treatment.

For delivery by inhalation, the active compound is preferably in the form of microparticles. They may be prepared by a variety of techniques, including spray-drying, freeze-drying and micronisation.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 (CCl2F2) and HFA-152 (CH4F2 and isobutane).

In a preferred embodiment of the invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 μm.

In the case of an aerosol-based formulation, a preferred composition is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

Compounds of the invention may be used in combination with other drugs that are used in the treatment/prevention/suppression or amelioration of the diseases or conditions for which present compounds are useful. Such other drugs may be administered, by a route and in an amount commonly used therefore, contemporaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the present invention include those that also contain one or more other active ingredients, in addition to a compound of the invention.

The agents of the invention may be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler or the inhalers for example as described EP-A-0505321).

Methods of Synthesis

The examples of the invention wherein $X^1-X^2$ is $-CR^{15}=N-$ can be prepared according to Schemes 1-4. Compounds wherein $X^1-X^2$ is $-NR^{19}-CO-$ can be prepared according to Schemes 5-10. Group $R^{15}$ and group $R^{19}$ is a group of formula $-[Y]_m-[Alk^1]_p-[Q]_r-[Alk^2]_q-Z$ or a group which can be later converted into such. For compounds wherein $X^1-X^2$ is $-CR^{15}=N-$ or $-NR^{19}-CO-$, further structural modifications may be made for example, but not exclusively, according to Scheme 11.

In Scheme 1, a 3-amino-1,2,4-triazole and a ketone with a beta electron-withdrawing group E (e.g. an ester, amide or ketone) may be reacted to form an intermediate (1), which can then be arylated with a suitable arylboronic acid, such as 3-(trifluoromethyl)phenylboronic acid, under copper catalysis to give examples of type (2). The reaction may be performed in the presence of base e.g. pyridine or triethylamine, either in the presence or absence of a solvent such as dichloromethane. All of the reactions may be performed in various solvents that must be compatible with the reagents used, and may be carried out at various suitable temperatures, typically 0-80° C., depending on the solvent used.

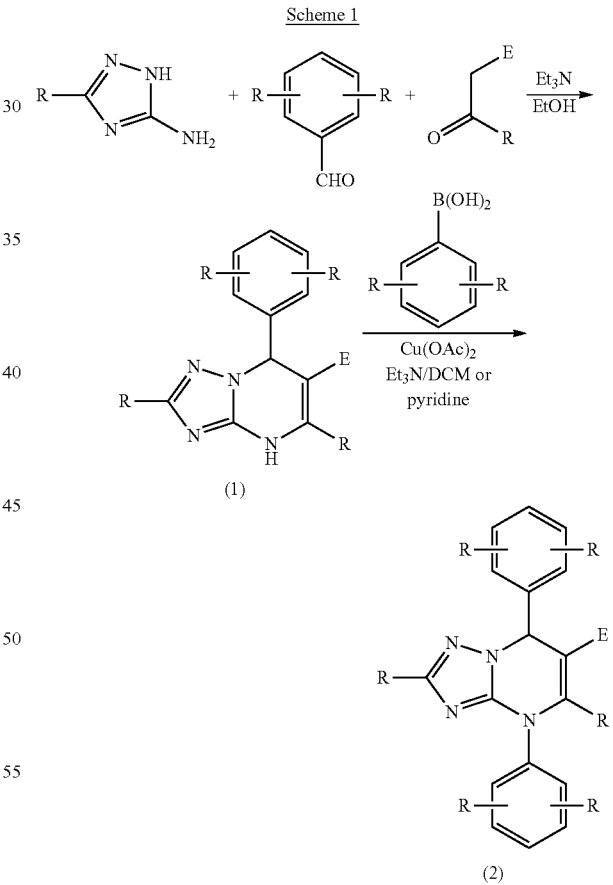

Scheme 1

The enantiomers of the racemic mixture (1) or (2) could be separated by chiral HPLC. Alternatively, where a carboxylic acid can be incorporated into the structure of (1) or (2) for example, but not exclusively, by the cleavage of a corresponding ester, resolution could be carried out by crystallisation with a chiral base (Schemes 2 and 3).

Scheme 2

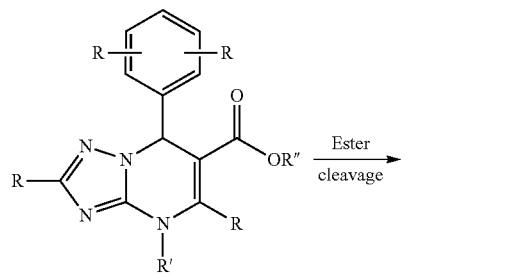

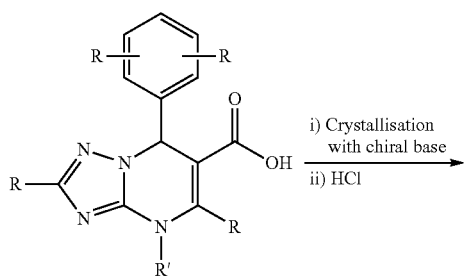

R' = H or Ar
R'' = e.g. allyl or benzyl

Scheme 3

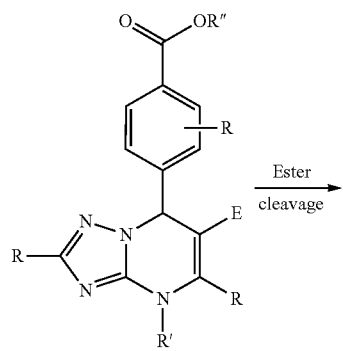

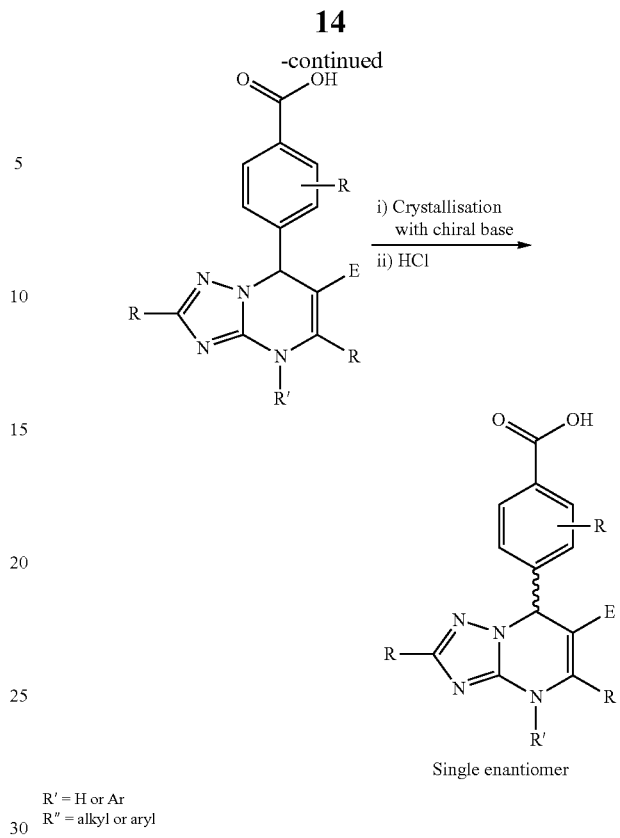

R' = H or Ar
R'' = alkyl or aryl

The three component reaction in Scheme 1 may also be carried out in a stereospecific manner using a chiral Lewis acid (Scheme 4) providing the required stereoisomer exclusively or in excess of its enantiomer (J. Am. Chem. Soc., 2005, 127, 16386-16387).

Scheme 4

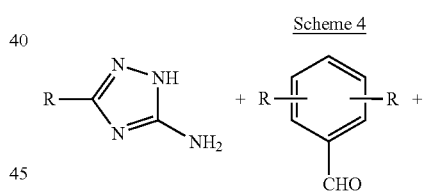

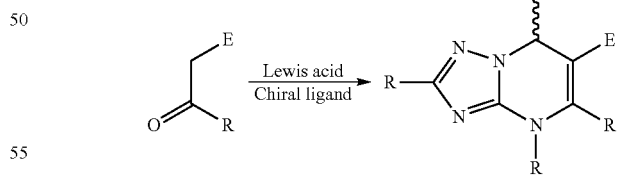

Other examples of the invention (6) can be prepared according to Scheme 5. O-Methylurea, an aldehyde and a ketone with a beta electron-withdrawing group E (e.g. an ester, amide or ketone) may be reacted in the presence of a base, such as sodium hydrogen carbonate, to form an intermediate (3). Reaction with an activated chloroformate, such as 4-nitrophenylchloroformate or pentafluorophenylchloroformate, produces (4). Ring closure can then be achieved using a substituted hydrazine to give (5). Arylation of (5) can be effected using an arylboronic acid, such as 3-(trifluoromethyl)phenylboronic acid, under copper catalysis and in the presence of a base e.g. pyridine or triethylamine. The reaction can be carried out with or without solvent. The group R may be removed under suitable conditions and when R'=H, the nitrogen atom may be alkylated or acylated using standard chemistry. All of the reactions may be performed in various solvents that must be compatible with the reagents used, and may be carried out at various suitable temperatures, typically 0-80° C., depending on the solvent used.

The enantiomers of racemic mixture (3), (5) or (6) may be separated by chiral HPLC. Schemes 6 to 9 show how the incorporation of a carboxylic acid group into a chiral intermediate may allow resolution by crystallisation of a chiral salt.

Scheme 5

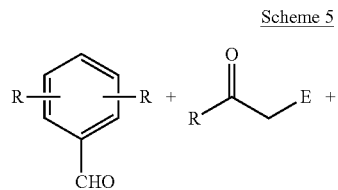

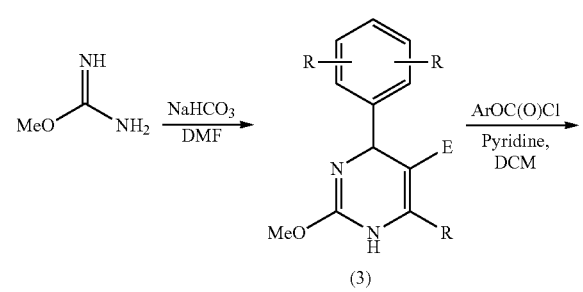

(3)

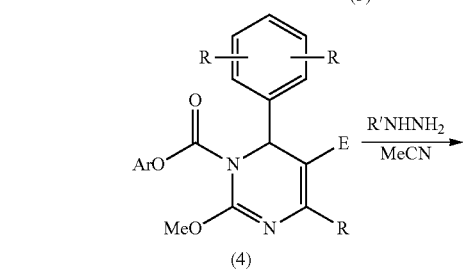

(4)

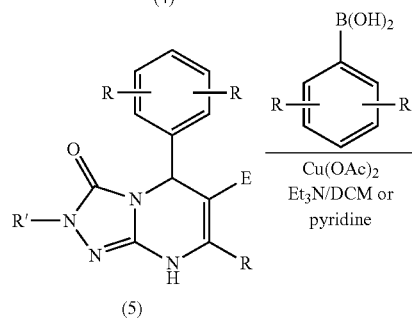

(5)

Scheme 6

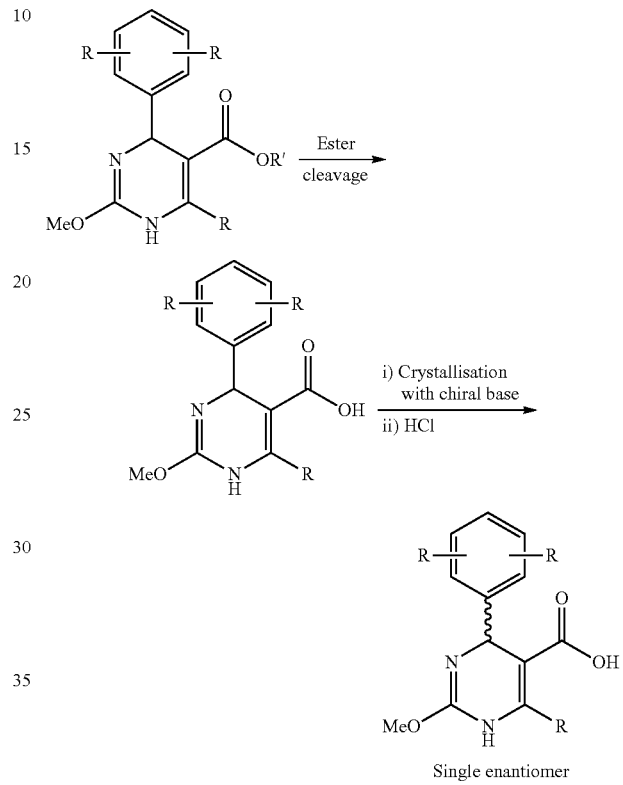

R' = alkyl or aryl

Scheme 7

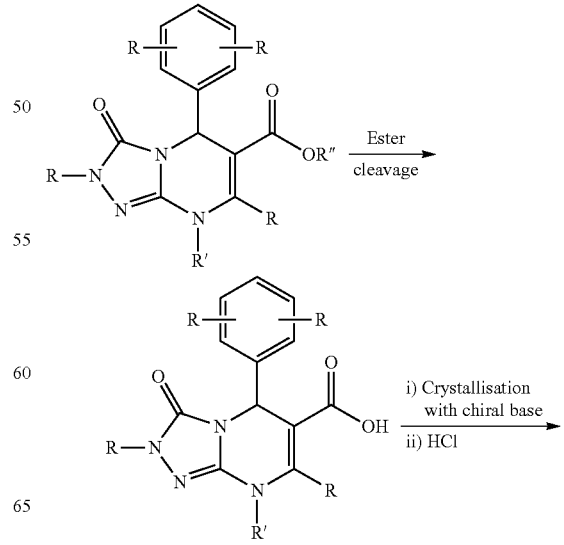

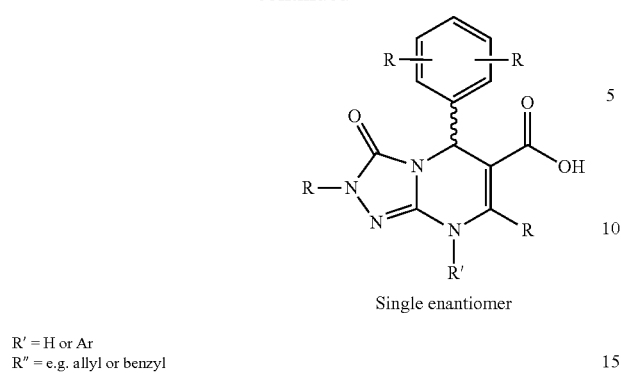

R' = H or Ar
R'' = e.g. allyl or benzyl

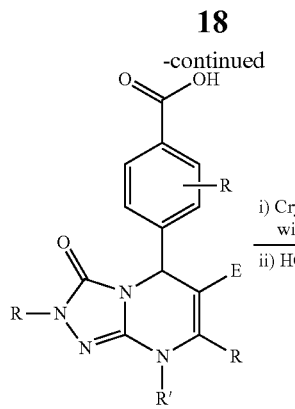

R' = H or Ar
R'' = alkyl or aryl

The three component reaction of Scheme 5 may also be carried out in a stereospecific manner providing exclusively, or an enantiomeric excess of, the more active enantiomer (Scheme 10) (J. Am. Chem. Soc., 2005, 127, 16386-16387).

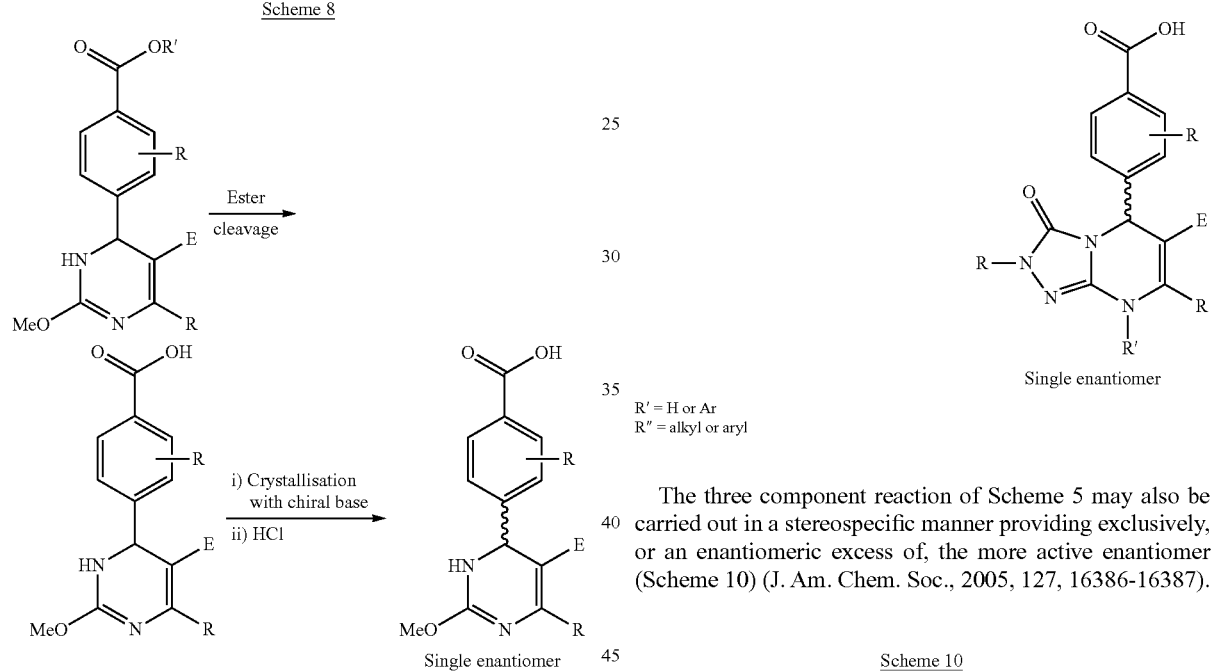

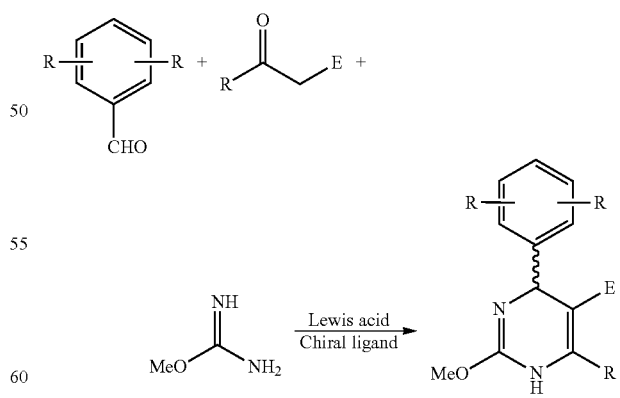

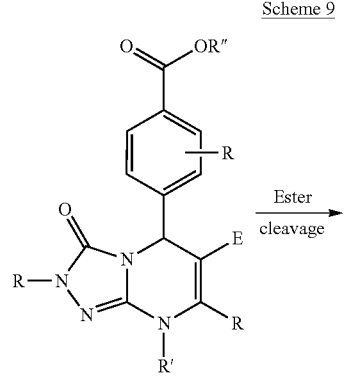

In Schemes 1, 3, 4, 5, 8, 9 and 10, E may be modified at various stages using standard chemical methods. Scheme 11 describes how, when group E is an ester, this functional group may be transformed using chemistries available to those skilled in the art.

Scheme 11: References (A) *Journal of the Indian Chemical Society*, 2007, 84(12), 1234-1238; (B) *Indian Journal of Heterocyclic Chemistry*, 2007, 16(4), 349-352; (C) *Indian Journal of Chemistry*, Section B: *Organic Chemistry Including Medicinal Chemistry*, 2003, 42B(4), 910-915; (D) *Indian Journal of Heterocyclic Chemistry*, 2004, 14(1), 43-46; (E) *Trends in Applied Sciences Research*, 2008, 3(2), 203-208; (F) *Acta Pharmaceutica* (Zagreb, Croatia), 2008, 58(1), 119-129.

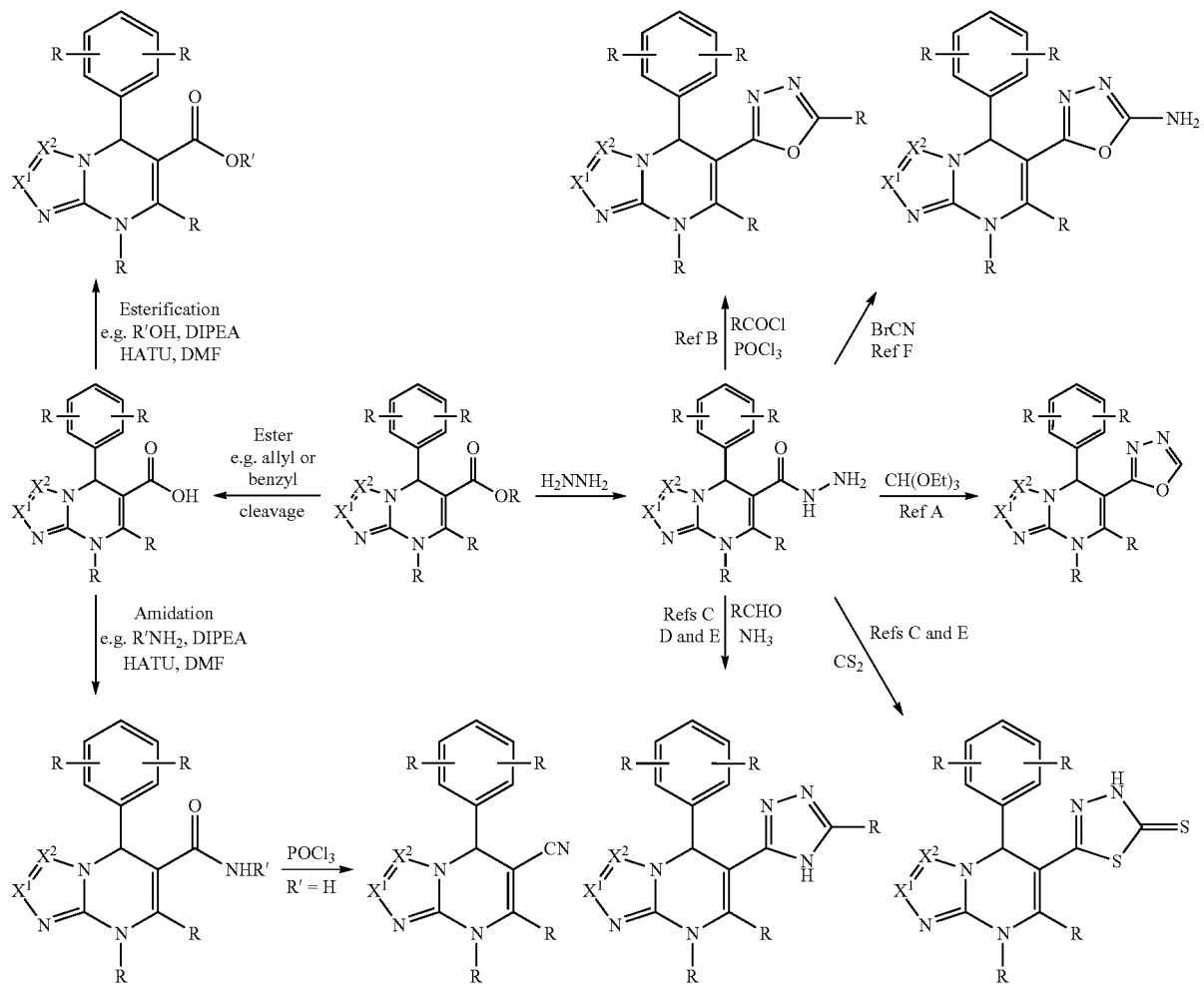

General Experimental Details

Reactions were not carried out under an inert atmosphere unless specified. Where products were purified using an Isolute® SPE Si II cartridge, 'Isolute SPE Si cartridge' refers to a pre-packed polypropylene column containing unbonded activated silica with irregular particles with average size of 50 m and nominal 60 Å porosity. Where an Isolute® SCX-2 cartridge was used, 'Isolute® SCX-2 cartridge' refers to a pre-packed polypropylene column containing a non end-capped propylsulphonic acid functionalised silica strong cation exchange sorbent. 'Isolute® PE-AX cartridge' refers to a pre-packed polypropylene column containing a silica-based sorbent with a chemically bonded quaternary ammonium functional group. All solvents and commercial reagents were used as received.

Preparative HPLC Conditions

HPLC System 1

C18-reverse-phase end-capped column (250×21.2 mm Gemini column with 5 μm particle size), eluting with a gradient of A: water; B: acetonitrile (0.1% formic acid added) with a flow rate typically 18 ml/min and gradient of 1%/min increasing in B. UV detection at 254 nm.

HPLC System 2

C18-reverse-phase end-capped column (250×21.2 mm Gemini column with 5 μm particle size), eluting with a gradient of A: water; B: methanol (0.1% formic acid added) with a flow rate typically 13 ml/min and gradient of 1%/min increasing in B. UV detection at 254 nm.

Analytical LC-MS Conditions

LC-MS Method 1

Waters Platform LC with a C18-reverse-phase column (30×4.6 mm Phenomenex Luna 3 μm particle size), elution with A: water+0.1% formic acid; B: acetonitrile+0.1% formic acid. Gradient:

| Gradient-Time | flow ml/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV
MS ionisation method—Electrospray (positive and negative ion)

LC-MS Method 2

Waters Micromass ZMD with a C18-reverse-phase column (30×4.6 mm Phenomenex Luna 3 μm particle size), elution with A: water+0.1% formic acid; B: acetonitrile+0.1% formic acid. Gradient:

| Gradient-Time | flow ml/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (100 μl split to MS with in-line UV detector)
MS ionisation method—Electrospray (positive and negative ion)

LC-MS Method 3

Waters Micromass ZQ2000 with a C18-reverse-phase column (100×2.1 mm Acquity BEH with 1.7 μm particle size) maintained at 40° C., elution with A: water+0.1% formic acid; B: acetonitrile+0.1% formic acid. Gradient:

| Gradient-Time | flow ml/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA
MS ionisation method—Electrospray (positive/negative ion)
Abbreviations used in the experimental section:
DCM dichloromethane
DIPEA Di-isopropylethylamine
DMF N,N-dimethylformamide
HATU O-(7-Azabenzotriazole-1-yl)-N,N,N',N'-tetramethyluronium hexafluoro-phosphate
HPLC high performance liquid chromatography
IMS Industrial methylated spirits
RT room temperature
Rt retention time Intermediate 1

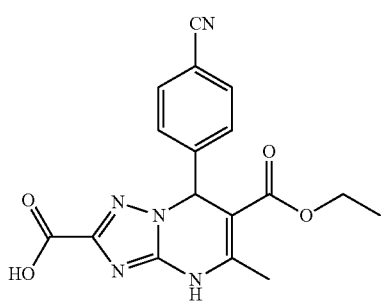 [SMILES: CCOC(=O)C1=C(C)Nc2nc(C(=O)O)nn2C1c1ccc(C#N)cc1]

7-(4-Cyanophenyl)-5-methyl-4,7-dihydro[1,2,4]triazolo[1,5a]pyrimidine-2,6-dicarboxylic acid 6-ethyl ester 3-Amino-1,2,4-triazole-5-carboxylic acid hydrate (2.56 g, 0.02 mol) was dissolved in IMS (40 ml). Triethylamine (6 ml) was added and the solution was heated to 70° C. After 10 minutes 4-cyanobenzaldehyde (2.62 g, 0.02 mol) and ethyl acetoacetate (2.60 g, 0.02 mol) were added and the reaction was heated at 70° C. for 24 hours. The mixture was filtered hot and allowed to cool. The volatiles were evaporated and the residue was partitioned between in ethyl acetate and 1N HCl. A solid precipitated and was filtered off. The organic layer was separated, washed with water and then brine, dried (Na$_2$SO$_4$), and evaporated. The residue was triturated with ethyl acetate. The solid material was combined with that which was collected earlier.

Yield: 2.18 mg (31%)
LC-MS (Method 1): Rt=2.69 min, m/z=354 [M+H]$^+$

Intermediate 2

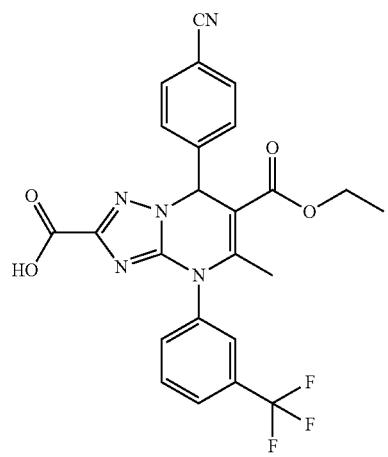 [SMILES: CCOC(=O)C1=C(C)N(c2cccc(C(F)(F)F)c2)c2nc(C(=O)O)nn2C1c1ccc(C#N)cc1]

7-(4-Cyanophenyl)-5-methyl-4-(3-trifluoromethylphenyl)-4,7-dihydro-[1,2,4]triazolo[1,5-a]pyrimidine-2,6-dicarboxylic acid 6-ethyl ester Intermediate 1 (1.90 g, 5.38 mmol), 3-(trifluoromethyl)phenylboronic acid (2.05 mg, 10.76 mmol), triethylamine (3 ml) and copper (II) acetate (1.32 g, 10.76 mmol) in DCM (10 ml) were stirred at RT for 6 days whilst being periodically opened to the air. The mixture was filtered through Celite® and the solvent was evaporated. The crude mixture was re-dissolved in DCM (10 ml) and further portions of the boronic acid, triethylamine and copper (II) acetate were added. After a further 5 days the reaction was diluted with DCM and 1N HCl. The biphasic mixture was filtered through Celite® and the organic layer was separated, washed with brine, dried (Na$_2$SO$_4$) and evaporated. The dark brown residue was chromatographed on an Isolute® SPE Si II cartridge (25 g) eluting with 0-100% EtOAc in pentane. Evaporation gave a solid which was triturated with diethyl ether to give the acid.
Yield: 472 mg (18%)
LC-MS (Method 1): Rt=3.63 min, m/z=498 [M+H]⁺

Intermediate 3

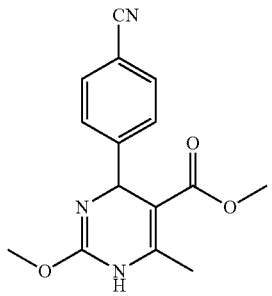

4-(4-Cyanophenyl)-2-methoxy-6-methyl-1,4-dihydropyrimidine-5-carboxylic acid methyl ester 4-Cyanobenzaldehyde (13.1 g, 100 mmol) was dissolved in DMF (200 ml) and sodium bicarbonate (33.4 g, 400 mmol) was added, followed by O-methylisourea hemisulphate (14.8 g, 120 mmol) and methyl acetoacetate (12.8 g, 110 mmol). The mixture was heated at 70° C. for 5 hours, then poured into water and the product extracted into ethyl acetate. The organic phase was washed with water (×2), then with brine and dried (Na₂SO₄). The solution was evaporated to dryness yielding a yellow gum. This was purified by silica gel chromatography using diethyl ether as eluent. Appropriate fractions were combined to yield the required product as a yellow solid.
Yield: 12.8 g (45%)
LC-MS (Method 1): Rt=2.20 min, m/z=286 [M+H]⁺

Intermediate 4

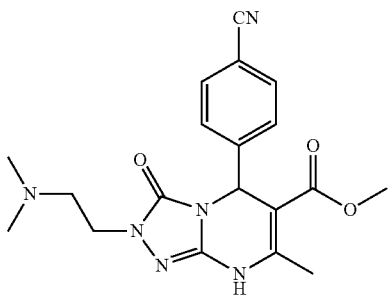

5-(4-Cyanophenyl)-2-(2-dimethylaminoethyl)-7-methyl-3-oxo-2,3,5,8-tetrahydro-[1,2,4]triazolo[4,3-a]pyrimidine-6-carboxylic acid methyl ester Intermediate 3 (1.0 g, 3.51 mmol) was dissolved in a mixture of DCM (15 ml) and pyridine (6 ml). The mixture was cooled in an ice bath and a solution of 4-nitrophenyl chloroformate (705 mg, 3.50 mmol) in DCM (15 ml) was added over 30 minutes. The reaction was stirred for 1 hour at 00° C. and then 2-(dimethylamino)ethylhydrazine dihydrochloride (618 mg, 3.51 mmol), triethylamine (2 ml) and acetonitrile (15 ml) were added and the reaction was allowed to warm to RT with stirring over 2 hours. The solvents were evaporated and residue was dissolved in methanol. The solution was loaded onto an Isolute® SCX-2 cartridge (20 g) which had been conditioned with methanol. The cartridge was flushed with methanol and then the product was eluted with 2M ammonia in methanol. Evaporation gave a yellow foam.
Yield: 655 mg (49%)
LC-MS (Method 2): Rt=0.28/1.73 min, m/z=383 [M+H]⁺

Intermediate 5

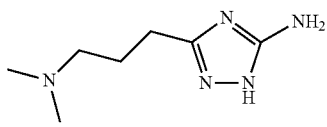

5-(3-Dimethylaminopropyl)-2H-[1,2,4]triazol-3-ylamine

Aminoguanidine bicarbonate (2.0 g, 14.71 mmol) was suspended in water (5 ml) and 4-(dimethylamine)butyric acid hydrochloride was added portionwise. After foaming had subsided, the pH was adjusted to pH 4 by the addition of conc. nitric acid. The reaction was heated under reflux for 48 hours before being allowed to cool. The water was evaporated and the residue treated with methanol. A small amount of solid material was removed by filtration and the solution was then eluted through an Isolute® PE-AX and an Isolute® SCX-2 cartridge. The solvent was removed to give Intermediate 5.

Intermediate 6

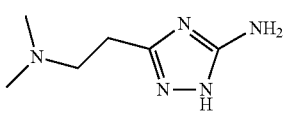

5-(2-Dimethylaminoethyl)-2H-[1,2,4]triazol-3-ylamine

Intermediate 6 was prepared using the method described for Intermediate 5.

Intermediate 7

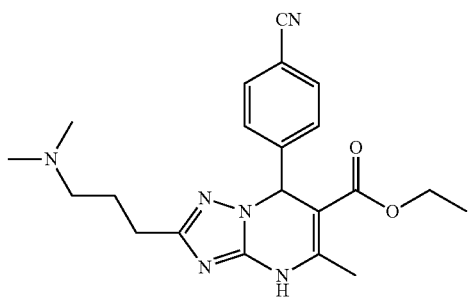 [SMILES: CCOC(=O)C1=C(C)Nc2nc(CCCN(C)C)nn2C1c1ccc(C#N)cc1]

7-(4-Cyanophenyl)-2-(3-dimethylaminopropyl)-5-methyl-4,7-dihydro[1,2,4]triazolo[1,5-a]pyrimidine-6-carboxylic acid ethyl ester 4-Cyanobenzaldehyde (1.98 g, 15 mmol), Intermediate 5 (2.55 g, 15 mmol), ethyl acetoacetate (1.96 g, 15 mmol) and triethylamine (4.18 ml, 23 mmol) were heated at 70° C. in IMS. After 24 hours the reaction mixture was allowed to cool and the solvent was evaporated. The residue was dissolved in methanol and the solution was loaded onto an Isolute® SCX-2 cartridge which had been conditioned with methanol. The cartridge was flushed with methanol and then the basic material was eluted with 2M ammonia in methanol. Evaporation gave a gum which was dissolved in ethyl acetate. Residual Intermediate 5 crystallised out and was removed by filtration. The mother liquor was concentrated and the crude product was purified on an Isolute® SPE Si II cartridge (10 g) eluting with 0-50% methanol in ethyl acetate. Intermediate 7 was obtained as a pale yellow solid.

Yield: 611 mg (10%)
LC-MS (Method 1): Rt=2.02 min, m/z=395 [M+H]$^+$

Intermediate 8

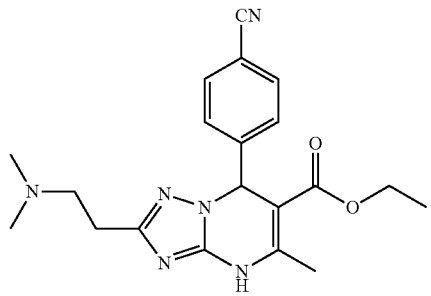 [SMILES: CCOC(=O)C1=C(C)Nc2nc(CCN(C)C)nn2C1c1ccc(C#N)cc1]

7-(4-Cyanophenyl)-2-(2-dimethylaminoethyl)-5-methyl-4,7-dihydro-[1,2,4]triazolo[1,5-a]pyrimidine-6-carboxylic acid ethyl ester Intermediate 8 was prepared from Intermediate 6 using the same method as that used for the synthesis of Intermediate 7.
LC-MS (Method 1): Rt=2.05 min, m/z=381 [M+H]$^+$

Example 1

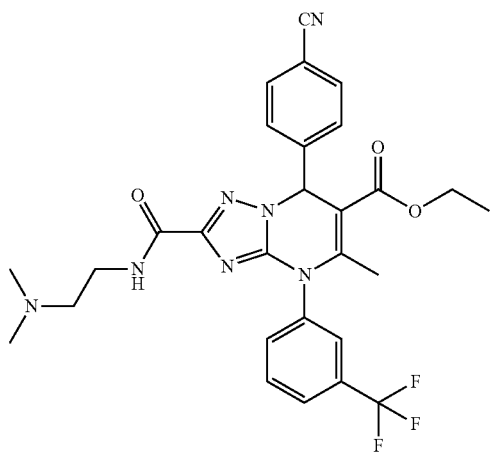 [SMILES: CCOC(=O)C1=C(C)N(c2cccc(C(F)(F)F)c2)c2nc(C(=O)NCCN(C)C)nn2C1c1ccc(C#N)cc1]

7-(4-Cyanophenyl)-2-(2-dimethylaminoethylcarbamoyl)-5-methyl-4-(3-trifluoromethylphenyl)-4,7-dihydro[1,2,4]triazolo[1,5-a]pyrimidine-6-carboxylic acid ethyl ester A mixture of Intermediate 2 (100 mg, 0.20 mmol), N,N-dimethylethylenediamine (27 mg, 0.30 mmol) and DIPEA (104 mg, 0.80 mmol) in DMF (3 ml) was treated with HATU (92 mg, 0.24 mmol). The reaction was stirred at RT for 4 hours and then the volatiles were evaporated. The residue was partitioned between ethyl acetate and sat. NaHCO$_3$(aq). The organic layer was separated, dried (Na$_2$SO$_4$) and evaporated. The crude product was purified using HPLC system 1 and obtained as a white solid.

Yield: 61 mg (54%)
LC-MS (Method 3): Rt=3.78 min, m/z=568.30 [M+H]$^+$

Example 2

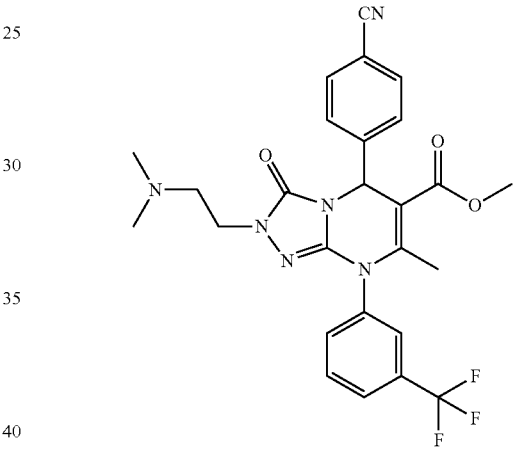

5-(4-Cyanophenyl)-2-(2-dimethylaminoethyl)-7-methyl-3-oxo-8-(3-trifluoromethylphenyl)-2,3,5,8-tetrahydro[1,2,4]triazolo[4,3-a]pyrimidine-6-carboxylic acid methyl ester Intermediate 4 (655 mg, 1.71 mmol), 3-(trifluoromethyl)phenylboronic acid (652 mg, 3.43 mmol) and copper (II) acetate (421 mg, 3.43 mmol) were dissolved in pyridine (25 ml). The reaction was heated at 55° C. open to air for 6 hours and then allowed to stand at RT for 17 hours. The solvents were evaporated and the residue was dissolved in methanol. The solution was loaded onto an Isolute® SCX-2 cartridge (20 g) which had been conditioned with methanol. The cartridge was flushed with methanol and then the product was eluted with 2M ammonia in methanol. The crude product was chromatographed on an Isolute® SPE Si II cartridge (10 g) eluting with 1:1 ethyl acetate/pentane. 40 mg of this semi-purified material was further purified using HPLC system 2. The product was obtained as a white solid.

Yield: 40 mg (4%)
LC-MS (Method 3): Rt=3.66 min, m/z=527.11 [M+H]$^+$

Example 3

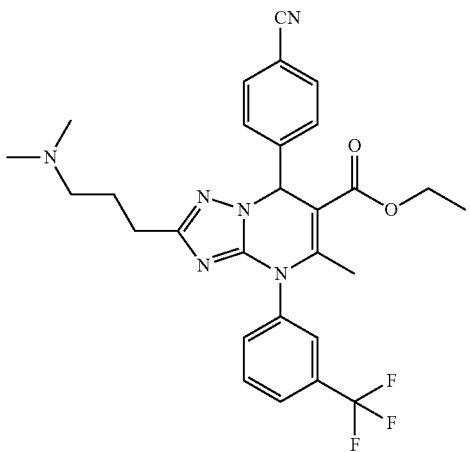 [SMILES: CCOC(=O)C1=C(C)N(c2cccc(C(F)(F)F)c2)c2nc(CCCN(C)C)nn2C1c1ccc(C#N)cc1]

7-(4-Cyanophenyl)-2-(3-dimethylaminopropyl)-5-methyl-4-(3-trifluoromethylphenyl)-4,7-dihydro-[1,2,4]triazolo[1,5-a]pyrimidine-6-carboxylic acid ethyl ester Intermediate 7 (200 mg, 0.51 mmol), 3-(trifluoromethyl)phenylboronic acid (193 mg, 1.02 mmol), copper (II) acetate (125 mg, 1.02 mmol) and triethylamine (206 mg, 2.04 mmol) were stirred under air at RT for 3 days. The volatiles were evaporated and the residue was dissolved in pyridine (3 ml). The reaction was allowed to stand in air at RT for 3 days and then heated at 50° C. overnight. The pyridine was evaporated and the residue was partitioned between DCM and 1M NaOH (aq). The organic layer was separated, washed with water, dried ($Na_2SO_4$) and evaporated to give a brown residue. The product was isolated using HPLC system 1. Example 3 was obtained as a white solid.

Yield: 9 mg (3%)

LC-MS (Method 3): Rt=3.82 min, m/z=539.26 $[M+H]^+$

Example 4

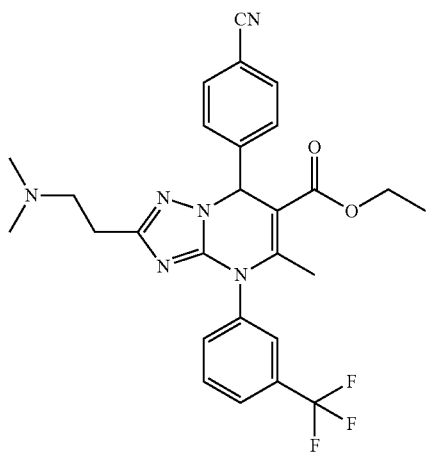 [SMILES: CCOC(=O)C1=C(C)N(c2cccc(C(F)(F)F)c2)c2nc(CCN(C)C)nn2C1c1ccc(C#N)cc1]

7-(4-Cyanophenyl)-2-(2-dimethylaminoethyl)-5-methyl-4-(3-trifluoromethyl phenyl)-4,7-dihydro[1,2,4]triazolo[1,5-a]pyrimidine-6-carboxylic acid ethyl ester Using the method used for the preparation of Example 3, Example 4 was prepared from Intermediate 8.

LC-MS (Method 3): Rt=3.81 min, m/z=525.26 $[M+H]^+$

Biological Assay

The compounds of the Examples were tested for HNE inhibitory activity.

Fluorescent Peptide Substrate

Assays were performed in 96-well plates at a total assay volume of 100 μl. The final concentration of the enzyme (human leukocyte elastase, Sigma E8140) was 0.00036 units/well. A peptide substrate (MeO-Suc-Ala-Ala-Pro-ValAMC, Calbiochem #324745) was used, at the final concentration of 100 μM. The final concentration of DMSO was 1% in the assay buffer (0.05M Tris.HCl, pH 7.5, 0.1M NaCl; 0.1M $CaC_2$; 0.0005% brij-35). The enzymatic reaction was started by adding the enzyme. The enzymatic reaction was performed at RT and after 30 mins stopped by adding 50 μl soybean trypsin inhibitor (Sigma T-9003) at a final concentration of 50 μg/well. Fluorescence was read on the FLEXstation (Molecular Devices) using 380 nm excitation and 460 nm emission filters. The potency of the compounds was determined from a concentration series of 10 concentrations in range from 1000 nM to 0.051 nM. The results are means of two independent experiments, each performed in duplicate.

The compounds had activity in the range 1-200 nM.

The invention claimed is:

1. A compound of formula (I):

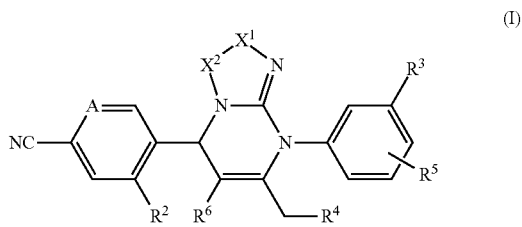

wherein

A is $C^1$—$R^1$ or N;

$R^1$ and $R^2$ are selected from hydrogen, halogen, nitro, cyano, —S(O)$_n$$R^7$, amino, mono- or di-$C_1$-$C_6$-alkylamino, —$NHCOR^8$, —NH(C=O)$NHR^9$, —$NHSO_2R^{10}$, $C_1$-$C_6$-alkyl, $C_2$-$C_6$-alkenyl, $C_2$-$C_6$-alkynyl, hydroxyl, $C_1$-$C_6$-alkoxy or $C_2$-$C_6$-alkenyloxy wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy;

n is 0, 1 or 2;

$R^4$ is hydrogen;

$R^3$ and $R^5$ are independently selected from hydrogen, halogen and $C_1$-$C_6$-alkyl which can be further substituted with halogen;

$R^6$ is selected from hydrogen, nitrile (—CN), —COOH, —$COOR^A$, —$COR^A$, —$SO_2R^A$—$CONH_2$, —$SO_2NH_2$, —$CONHR^A$, —$SO_2NHR^A$, $CONR^AR^B$, $SO_2NR^AR^B$ and heteroaryl, wherein $R^A$ and $R^B$ are independently an optionally substituted ($C_1$-$C_6$)alkyl, phenyl or monocyclic heteroaryl having 5 or 6 ring atoms, or $R^A$ and $R^B$ when attached to the same nitrogen atom form a cyclic amino ring;

$R^7$ is selected from $C_1$-$C_6$-alkyl, hydroxy-$C_1$-$C_6$-alkyl, $C_1$-$C_4$-alkoxy, amino, mono- or di-$C_1$-$C_4$-alkylamino, hydroxycarbonyl, aminocarbonyl, $C_3$-$C_6$-cycloalkyl, phenyl or $C_2$-$C_6$-alkenyl; wherein $C_3$-$C_6$-cycloalkyl can be substituted with one or more of $C_1$-$C_4$-alkyl, hydroxyl and $C_1$-$C_4$-alkoxy and phenyl can be substituted with one or more of halogen, cyano, $C_1$-$C_4$-alkyl, difluoromethyl, trifluoromethyl, difluoromethoxy, trifluoromethoxy and $C_1$-$C_4$-alkoxy;

$R^8$ and $R^9$ are independently selected from hydrogen and $C_1$-$C_6$-alkyl, and $R^{10}$ is $C_1$-$C_6$ alkyl;

—$X^1$—$X^2$— is —$NR^{19}$—CO—;

$R^{15}$ and $R^{19}$ each independently represent a radical of formula —$[Y]_m$-$[Alk^1]_p$-$[Q]_t$-$[Alk^2]_q$-Z, wherein Y is —O—, —S—, —$NR^E$—, —(C=O)—, —S(O)$_2$—, —C(=O)O—, —(C=O)$NR^E$—, —$NR^E$(C=O)—, —$NR^E$—$C_1$-$C_4$-alkyl-, or —$C_1$-$C_4$-alkyl-$NR^E$—, —S(O)$_2NR^E$—, —$NR^ES(O)_2$— wherein $R^E$ is hydrogen, $C_1$-$C_6$ alkyl;

m, p, q and t are independently 0 or 1;

$Alk^1$ and $Alk^2$ each independently represent a $C_1$-$C_6$ alkylene radical;

Q represents a divalent mono- or bicyclic carbocyclic or heterocyclic radical having 3-9 ring members;

Z is (i) a monocyclic heterocyclic ring of 5 or 6 ring members or a bridged heterocyclic ring system of 7 or 8 ring members, wherein the ring heteroatoms are nitrogen, said monocyclic ring or bridged ring system being linked to the rest of the molecule via a ring carbon, and wherein a ring nitrogen may be quaternized by substitution by $C_1$-$C_3$ alkyl or benzyl the latter being optionally substituted in the phenyl ring thereof; or (ii) —N($R^A$)($R^B$) wherein $R^A$ and $R^B$ are independently hydrogen, or a $C_1$-$C_6$-alkyl, $C_3$-$C_6$-cycloalkyl group, or a phenyl($C_1$-$C_6$)alkyl- group optionally substituted in the phenyl ring thereof; or, taken together with the nitrogen to which they are attached form a monocyclic heterocyclic ring of 5 to 7 ring atoms which may contain a further heteroatom selected from N, O and S; or (iii) —$N_+$($R^A$)($R^B$)($R^C$) wherein $R^A$, $R^B$ and $R^C$ are independently a $C_1$-$C_6$-alkyl, $C_3$-$C_6$-cycloalkyl group, or a phenyl($C_1$-$C_6$)alkyl- group optionally substituted in the phenyl ring thereof; or $R^A$ is a $C_1$-$C_6$-alkyl, $C_3$-$C_6$-cycloalkyl group, or a phenyl($C_1$-$C_6$)alkyl- group optionally substituted in the phenyl ring thereof and $R^B$ and $R^C$ taken together with the nitrogen to which they are attached form a monocyclic heterocyclic ring of 5 to 7 ring atoms which may contain a further heteroatom selected from N, O and S; or $R^A$, $R^B$ and $R^C$ taken together with the nitrogen to which they are attached form a bridged heterocyclic ring system of 7 or 8 ring members;

(iv) —$NR^AC$(=$NR^B$)$NR^CR^D$ wherein $R^A$, $R^B$, $R^C$ and $R^D$ are independently hydrogen or $C_1$-$C_6$-alkyl; or any two of $R^A$, $R^B$, $R^C$ and $R^D$ are independently hydrogen or $C_1$-$C_6$-alkyl, while the other two taken together represent a $C_1$-$C_6$ alkylene radical; or (v) —C(=$NR^A$)$NR^BR^C$, wherein $R^A$, $R^B$ and $R^C$ are independently hydrogen or $C_1$-$C_6$-alkyl; or any one of $R^A$, $R^B$ and $R^C$ is hydrogen or $C_1$-$C_6$-alkyl, while the other two taken together represent a $C_1$-$C_6$ alkylene radical;

(vi) —$NR^AC$(=$NR^C$)$R^B$, wherein $R^A$, $R^B$ and $R^C$ are independently hydrogen or $C_1$-$C_6$-alkyl; or any one of $R^A$, $R^B$ and $R^C$ is hydrogen or $C_1$-$C_6$-alkyl, while the other two taken together represent a $C_1$-$C_6$ alkylene radical, or a pharmaceutically acceptable salt thereof.

2. A compound or pharmaceutically acceptable salt as claimed in claim 1 wherein $R^2$ is hydrogen or methanesulphonyl.

3. A compound or pharmaceutically acceptable salt as claimed in claim 1, wherein $R^5$ hydrogen and $R^3$ is 3-trifluoromethyl, 3-chloro or 3-bromo.

4. A compound or pharmaceutically acceptable salt as claimed in claim 1, wherein $R^{15}$ and $R^{19}$ have the formula -$[Alk^1]_p$-$[Q]_t$-$[Alk^2]_q$-Z wherein -$[Alk^1]_p$-$[Q]_t$-$[Alk^2]_q$- is selected from structures (IV) and (V) wherein $V^1$ and $V^2$ are each independently 0, 1, 2, 3 or 4 and X is a divalent mono- or bicyclic carbocyclic or heterocyclic radical having 3-9 ring members, and Z is selected from structures (VI)-(XIV) wherein $R^A$, $R^B$, $R^C$, and $R^D$ are as defined in claim 1, and $V^1$, $V^2$, and $V^3$ are each independently 0, 1, 2, 3 or 4:

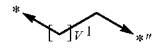

(IV)

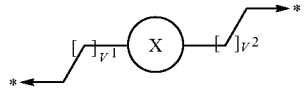

(V)

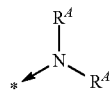

(VI)

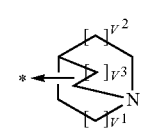

(VII)

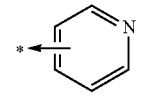

(VIII)

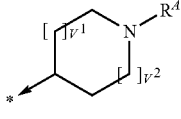

(IX)

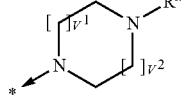

(X)

(XI) 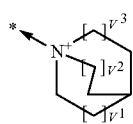

(XII) 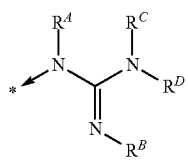

(XIII) 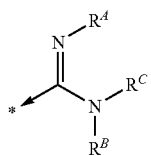

(XIV) 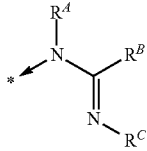

and wherein amine and pyridine nitrogen atoms, where present in groups (VI)-(XIV), may be quaternized.

5. A compound or pharmaceutically acceptable salt as claimed in claim 1, wherein $R^{15}$ and $R^{19}$ each independently represent a radical of formula —[Y]$_m$-Alk$^2$-Z, wherein Y is —(C=O)—; m is 0 or 1; Alk$^2$ is a $C_1$-$C_6$ alkylene radical; and Z is —N(R$^A$)(R$^B$) wherein R$^A$ and R$^B$ are independently $C_1$-$C_4$-alkyl, or R$^A$ is hydrogen and R$^B$ is $C_1$-$C_4$-alkyl.

6. A compound or pharmaceutically acceptable salt as claimed in claim 1, in wherein $R^6$ is —COOR$^A$, wherein R$^A$ is $C_1$-$C_4$ alkyl.

7. A compound or pharmaceutically acceptable salt as claimed in claim 1, which is in the form of a pharmaceutically acceptable salt.

8. A pharmaceutical composition comprising a compound or pharmaceutically acceptable salt as claimed in claim 1, and a pharmaceutically acceptable carrier or excipient.

9. A pharmaceutical composition as claimed in claim 8 which is adapted for oral administration or administration by the pulmonary route.

* * * * *